United States Patent
Takeda

(10) Patent No.: US 11,494,878 B2
(45) Date of Patent: Nov. 8, 2022

(54) IMAGE PROCESSING DEVICE PERFORMING A PROCESS FOR REDUCING NOISE INCLUDED IN A RADIATION IMAGE

(71) Applicant: Shimadzu Corporation, Kyoto (JP)

(72) Inventor: Ryo Takeda, Kyoto (JP)

(73) Assignee: Shimadzu Corporation, Kyoto (JP)

(*) Notice: Subject to any disclaimer, the term of this patent is extended or adjusted under 35 U.S.C. 154(b) by 55 days.

(21) Appl. No.: 16/642,331

(22) PCT Filed: Sep. 1, 2017

(86) PCT No.: PCT/JP2017/031527
§ 371 (c)(1),
(2) Date: Feb. 26, 2020

(87) PCT Pub. No.: WO2019/043901
PCT Pub. Date: Mar. 7, 2019

(65) Prior Publication Data
US 2021/0073951 A1 Mar. 11, 2021

(51) Int. Cl.
*G06K 9/40* (2006.01)
*G06T 5/00* (2006.01)
*A61B 6/00* (2006.01)
*G06T 5/20* (2006.01)

(52) U.S. Cl.
CPC ............ *G06T 5/002* (2013.01); *A61B 6/5282* (2013.01); *G06T 5/20* (2013.01); *G06T 2207/10116* (2013.01); *G06T 2207/20182* (2013.01)

(58) Field of Classification Search
None
See application file for complete search history.

(56) References Cited

U.S. PATENT DOCUMENTS

| | | | | |
|---|---|---|---|---|
| 5,771,269 A | * | 6/1998 | Chao | A61B 6/4035 378/147 |
| 6,134,297 A | * | 10/2000 | Chao | A61B 6/06 378/98.12 |
| 8,064,676 B2 | | 11/2011 | Li et al. | |
| 9,943,282 B2 | * | 4/2018 | Katsumata | G06T 5/002 |
| 11,054,534 B1 | * | 7/2021 | Nutt | A61B 6/4266 |
| 2009/0225932 A1 | * | 9/2009 | Zhu | G06T 11/005 378/98.12 |

(Continued)

FOREIGN PATENT DOCUMENTS

| JP | 2015-167613 A | 9/2015 |
|---|---|---|
| JP | 2016-202219 A | 12/2016 |

(Continued)

OTHER PUBLICATIONS

Written Opinion by the International Search Authority for PCT application PCT/JP2017/031527, dated Oct. 10, 2017, submitted with a machine translation.

*Primary Examiner* — Randolph I Chu
(74) *Attorney, Agent, or Firm* — Muir Patent Law, PLLC

(57) ABSTRACT

An image processing device (100) includes a noise reducer (22) including a pixel ratio acquirer (23) configured to acquire a pixel value ratio ($\alpha$) between a scattered-ray reduced image (52) after reduction of a scattered-ray component and a radiation image (51) before the reduction of the scattered-ray component, the noise reducer being configured to reduce a noise component from the scattered-ray reduced image based on the pixel value ratio.

4 Claims, 7 Drawing Sheets

(56) References Cited

U.S. PATENT DOCUMENTS

| | | | |
|---|---|---|---|
| 2010/0104165 A1* | 4/2010 | Takahashi | A61B 6/5282 |
| | | | 382/132 |
| 2015/0063526 A1* | 3/2015 | Kobayashi | A61B 6/5282 |
| | | | 378/62 |
| 2016/0140721 A1* | 5/2016 | Kawamura | A61B 6/466 |
| | | | 382/132 |
| 2016/0302752 A1 | 10/2016 | Ito et al. | |
| 2016/0354052 A1 | 12/2016 | Kawanishi | |
| 2017/0000443 A1* | 1/2017 | Katsumata | G06T 5/50 |
| 2017/0065244 A1 | 3/2017 | Taki | |
| 2017/0364635 A1* | 12/2017 | Kobayashi | G06F 16/5838 |
| 2018/0185002 A1 | 7/2018 | Katsumata | |

FOREIGN PATENT DOCUMENTS

| | | |
|---|---|---|
| JP | 2017-012445 A | 1/2017 |
| JP | 2017-051395 A | 3/2017 |

\* cited by examiner

IMAGE PROCESSING DEVICE PERFORMING A PROCESS FOR REDUCING NOISE INCLUDED IN A RADIATION IMAGE

TECHNICAL FIELD

The present invention relates to an image processing device, and more particularly, it relates to an image processing device configured to perform a process for reducing noise included in a radiation image.

BACKGROUND ART

Conventionally, an image processing device configured to perform a process for reducing noise included in a radiation image is known. Such an image processing device is disclosed in Japanese Patent Laid-Open No. 2017-12445, for example.

A radiation image includes a component due to a direct ray (primary radiation) transmitted through a subject from a radiation source and directly detected by a detector, a component due to a scattered ray scattered in the subject and detected by the detector, and a noise component. The noise component includes statistical noise (quantum noise) derived from statistical fluctuation when radiation photons are detected by the detector.

An image processing device disclosed in Japanese Patent Laid-Open No. 2017-12445 includes an estimation unit configured to estimate a scattered-ray component included in a radiation image, a noise reduction unit configured to reduce a noise component included in the radiation image, and an output unit.

In Japanese Patent Laid-Open No. 2017-12445, a scattered-ray reduced image is acquired by subtracting the scattered-ray component estimated by the estimation unit from the radiation image. The noise reduction unit acquires first noise statistics from the radiation image and second noise statistics from the scattered-ray reduced image. The noise statistics are standard deviations for each image based on pixel values of each of the images, and the correlation between a certain pixel and a noise statistic included in the certain pixel is obtained in advance and stored in a storage device (look-up table). The noise reduction unit performs an image process to reduce a noise component based on the first noise statistics and the second noise statistics. Thus, a corrected image obtained by reducing the scattered-ray component and the noise component from the radiation image is output.

PRIOR ART

Patent Document

Patent Document 1: Japanese Patent Laid-Open No. 2017-12445

SUMMARY OF THE INVENTION

Problem to be Solved by the Invention

However, in Japanese Patent Laid-Open No. 2017-12445, in order to acquire the noise statistics, it is necessary to perform a process for obtaining the correlation of the noise statistic in advance for each pixel, and it is necessary to acquire the first noise statistics and the second statistics, referring to the storage device when the image process is performed. Thus, due to the complicated noise reduction process and high computational cost (computational load), the process is disadvantageously likely to slow down (the processing load is likely to be heavy).

The present invention is intended to solve the above problem. The present invention aims to provide an image processing device capable of simplifying a noise reduction process and performing the noise reduction process at high speed and at low computational cost (computational load).

Means for Solving the Problem

In order to attain the aforementioned object, an image processing device according to an aspect of the present invention includes a scattered-ray reducer configured to reduce, from a radiation image, a scattered-ray component included in the radiation image obtained by irradiating a subject with radiation, and a noise reducer configured to reduce a noise component included in a scattered-ray reduced image obtained by reducing the scattered-ray component from the radiation image, the noise reducer including a pixel ratio acquirer configured to acquire a pixel value ratio between the scattered-ray reduced image after reduction of the scattered-ray component and the radiation image before the reduction of the scattered-ray component, the noise reducer being configured to reduce the noise component from the scattered-ray reduced image based on the pixel value ratio. Furthermore, the image processing device is configured to output a corrected image obtained by reducing the scattered-ray component and the noise component from the radiation image.

In this specification, the radiation is X-rays, for example, but it indicates a broader concept including radiation other than X-rays, such as gamma rays and particle rays. The radiation image is an image obtained by irradiating the subject with the radiation and detecting the radiation transmitted through the subject with a detector. The noise component is a noise component included in the radiation image, and indicates a concept including a noise component caused by statistical noise (quantum noise) derived from statistical fluctuation when radiation photons are detected by the detector. It is known that the statistical noise (statistical noise amount) has a positive correlation with the amount of radiation that has reached the detector (i.e., a pixel value of the radiation image). The noise component reduced by the noise reducer according to the present invention is noise correlated with the pixel value of the radiation image, like the statistical noise, and may include noise other than the statistical noise as long as the noise correlates with the pixel value. Noise that does not correlate with the pixel value, such as electrical noise of the detector (detection circuit), is not included. The pixel value ratio between the scattered-ray reduced image (Sc) and the radiation image (In) includes a ratio represented by (Sc/In). The pixel value ratio may be an inverse ratio (In/Sc) as long as the ratio represents a change in pixel value before and after reduction of the scattered-ray component using the respective pixel values of the scattered-ray reduced image and the radiation image. This indicates a broader concept that allows a ratio in the form of a ratio of change in pixel value (|In−Sc|/In).

In the image processing device according to this aspect of the present invention, as described above, the noise reducer includes the pixel ratio acquirer configured to acquire the pixel value ratio between the scattered-ray reduced image after the reduction of the scattered-ray component and the radiation image before the reduction of the scattered-ray component, and is configured to reduce the noise component from the scattered-ray reduced image based on the pixel value ratio. The statistical noise has a correlation with the pixel value of the radiation image, and thus the scattered dose can be associated with a noise component amount (noise component amount to be reduced) according to the scattered dose using the pixel value ratio between the scattered-ray reduced image and the radiation image. Therefore, the noise component can be appropriately reduced from the radiation image by a simple process based on the pixel value ratio. Thus, unlike the related art, it is not necessary to separately acquire noise statistics from the radiation image and the scattered-ray reduced image, and the noise component can be simply reduced based on the pixel value ratio between the radiation image and the scattered-ray reduced image. Consequently, the noise reduction process can be simplified, and can be performed at high speed and at low computational cost.

In the aforementioned image processing device according to this aspect, the noise reducer preferably includes a synthesis weight setter configured to set a synthesis weight based on the pixel value ratio, and a synthesizer configured to perform weighted synthesis on a noise reduced image obtained by reducing the noise component from the scattered-ray reduced image and the scattered-ray reduced image using the synthesis weight that has been set. With this configuration, when the noise reduction effect is weakened, the synthesis weight of the scattered-ray reduced image is increased, and when the noise reduction effect is enhanced, the synthesis weight of the noise reduced image is increased such that the degree of reduction of the noise component can be adjusted. Furthermore, the synthesis weight can be set according to the noise component amount (noise component amount to be reduced) grasped based on the pixel value ratio, and thus an appropriate noise reduction process can be performed according to the noise component amount included in the scattered-ray reduced image while the computational cost is reduced based on the pixel value ratio.

In this case, the synthesis weight setter is preferably configured to set the synthesis weight in such a manner that as the pixel value ratio of the scattered-ray reduced image to the radiation image decreases, a weight of the noise reduced image increases. When the pixel value ratio of the scattered-ray reduced image to the radiation image is small, it means that the scattered dose included in the radiation image is large, and thus the noise component amount correlated with the detected scattered dose is large. On the other hand, when the pixel value ratio is large, the noise component amount is small. Therefore, as the pixel value ratio is smaller, synthesis is performed with the larger weight of the noise reduced image such that the noise component can be effectively reduced according to the noise component amount.

In the aforementioned configuration in which the noise reducer includes the synthesis weight setter and the synthesizer, the synthesis weight setter is preferably configured to set a weight of the scattered-ray reduced image to zero when the pixel value ratio of the scattered-ray reduced image to the radiation image is smaller than a threshold. In the noise component reduction process, as the noise reduction effect is enhanced, a non-noise component (information to be imaged) is also removed, and thus the noise reduction effect is limited. Therefore, if the noise reduced image is generated with a noise reduction effect that does not excessively remove the non-noise component, the noise reduced image is directly output when the noise component amount is so large that the pixel value ratio is smaller than the threshold such that the limit of the noise reduction effect can be set in a range in which the image quality is not excessively reduced without increasing the computational cost.

The aforementioned image processing device according to this aspect preferably further includes a band image acquirer configured to frequency-decompose the scattered-ray reduced image to acquire a plurality of band images of a plurality of frequency bands, and a band image synthesizer configured to synthesize a plurality of corrected band images obtained by reducing the noise component included in each of the plurality of band images. The noise reducer is preferably configured to reduce the noise component for each of the plurality of band images based on the pixel value ratio. With this configuration, the noise reduction process based on the pixel value ratio can be performed on each of the plurality of band images for each band. Consequently, it is possible to obtain the corrected image on which an appropriate noise reduction process has been performed for each frequency band.

In this case, the noise reducer preferably includes a synthesis weight setter configured to separately set a synthesis weight for each of the plurality of band images based on the pixel value ratio, and a synthesizer configured to perform weighted synthesis on a noise reduced image obtained by reducing the noise component from each of the plurality of band images and a corresponding band image using the synthesis weight set for each of the plurality of band images. With this configuration, the noise reduction effect can be adjusted for each band, and thus flexible image quality adjustment becomes possible.

Effect of the Invention

According to the present invention, as described above, it is possible to simplify the noise reduction process and perform the noise reduction process at high speed and at low computational cost.

MODES FOR CARRYING OUT THE INVENTION

Embodiments embodying the present invention are hereinafter described on the basis of the drawings.

First Embodiment

An image processing device 100 according to a first embodiment of the present invention is applied to an X-ray imaging apparatus 1, for example, and performs an image process on an X-ray image captured by the X-ray imaging apparatus 1. The overall configuration of the X-ray imaging apparatus 1 is now described with reference to FIG. 1. The X-ray image is an example of a "radiation image" in the claims.

(Configuration of X-ray Imaging Apparatus)

Figure 1:
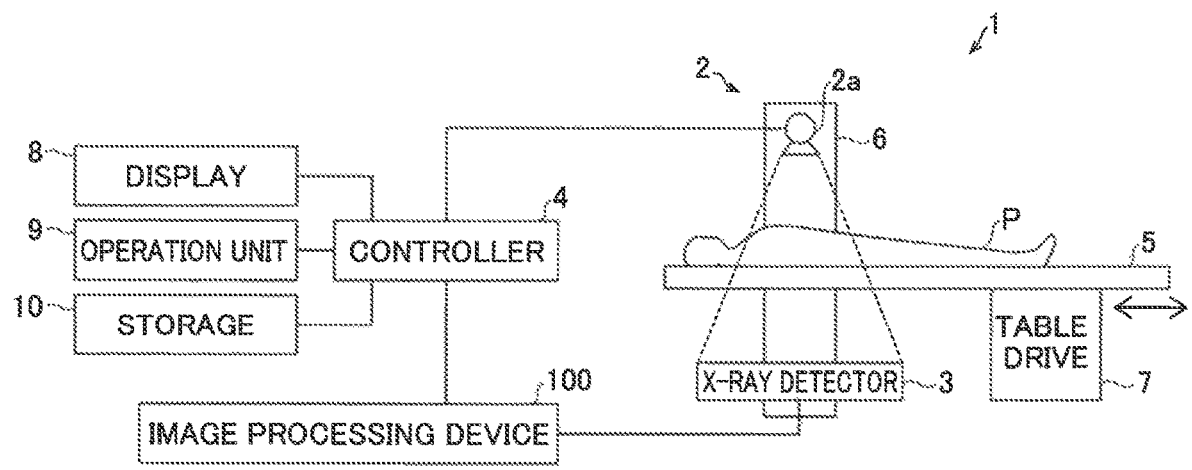
FIG. 1 is a schematic view showing an X-ray imaging apparatus including an image processing device according to a first embodiment.

As shown in FIG. 1, the X-ray imaging apparatus 1 is an apparatus that captures an X-ray image as a transmission image of the inside of a subject P by irradiating the subject P with X-rays and detecting the X-rays transmitted through the subject P. The X-ray imaging apparatus 1 is an X-ray diagnostic apparatus (medical X-ray apparatus) used for clinical diagnosis in the medical field. The subject P is mainly a human (patient). The image processing device 100 according to this embodiment may be applied to an industrial X-ray imaging apparatus used for non-destructive inspection, for example, in addition to the medical X-ray apparatus.

The X-ray imaging apparatus 1 includes an X-ray irradiator 2 that irradiates the subject P with X-rays, an X-ray detector 3 that detects the X-rays transmitted through the subject P, a controller 4, and the image processing device 100.

The X-ray irradiator 2 and the X-ray detector 3 are arranged in such a manner as to face each other with a table 5, on which the subject P is placed, interposed therebetween. The X-ray irradiator 2 and the X-ray detector 3 are movably supported by a moving mechanism 6. The table 5 is movable in a horizontal direction by a table drive 7. The X-ray irradiator 2, the X-ray detector 3, and the table 5 are moved via the moving mechanism 6 and the table drive 7 such that a region of interest of the subject P can be imaged. The moving mechanism 6 and the table drive 7 are controlled by the controller 4.

The X-ray irradiator 2 includes an X-ray tube 2a that generates X-rays when power is supplied thereto, and is connected to a high-voltage generator (not shown). The X-ray tube 2a is arranged in such a manner that its X-ray emission direction faces a detection surface of the X-ray detector 3. The X-ray irradiator 2 is connected to the controller 4. The controller 4 controls the X-ray irradiator 2 in accordance with preset imaging conditions such as a tube voltage, a tube current, and an X-ray irradiation time, and generates X-rays from the X-ray tube 2a.

The X-ray detector 3 detects the X-rays radiated from the X-ray irradiator 2 and transmitted through the subject P, and outputs a detection signal corresponding to the detected X-ray intensity. The X-ray detector 3 includes a flat panel detector (FPD), for example. The X-ray detector 3 outputs an X-ray image (detection signal) having a predetermined resolution to the image processing device 100.

In a configuration example of FIG. 1, an apparatus is shown in which X-ray imaging is performed while the X-ray irradiator 2 and the X-ray detector 3 face each other in an upward-downward direction with the table 5 interposed therebetween, and the subject is placed on the table 5 in a recumbent position (lying position) or a seated position (sitting position). The X-ray imaging apparatus 1 may be an apparatus that performs X-ray imaging while the X-ray irradiator 2 and the X-ray detector 3 horizontally face each other, and the subject is placed in an upright position (standing position) between the X-ray irradiator 2 and the X-ray detector 3, or an apparatus that can perform imaging in any of a recumbent position, a seated position, and an upright position.

The controller 4 includes a central processing unit (CPU), a read only memory (ROM), a random access memory (RAM), etc. The CPU functions as a controller that controls each portion of the X-ray imaging apparatus 1 by executing a predetermined control program. The controller 4 controls the X-ray irradiator 2 and controls the driving of the moving mechanism 6 and the table drive 7.

In the example of FIG. 1, the X-ray imaging apparatus 1 includes a display 8, an operation unit 9, and a storage 10. The display 8 is a monitor such as a liquid crystal display. The operation unit 9 includes a keyboard and a mouse, a touch panel, or another control, for example. The storage 10 includes a storage device such as a hard disk drive. The controller 4 is configured to control the display 8 to display an image generated by the image processing device 100. The controller 4 is configured to receive an input operation via the operation unit 9. Furthermore, the controller 4 is configured to control the storage 10 to store image data, the imaging conditions, and various setting values.

The image processing device 100 acquires an X-ray detection signal from the X-ray detector 3 and generates an X-ray image. The image processing device 100 performs the image process on the acquired X-ray image. The image process includes a correction process such as a process for reducing scattered-ray components included in the X-ray image and a process for reducing noise components included in the X-ray image. Although the description is omitted, the image processing device 100 performs a known correction process, for example, in addition to the process for reducing the scattered-ray components and the noise components. The image processing device 100 outputs the corrected image, which is the X-ray image after the image process, to the controller 4. The corrected image is displayed on the display 8 or recorded in the storage 10. The X-ray image is a still image or a moving image.

(Configuration of Image Processing Device)

Figure 2:
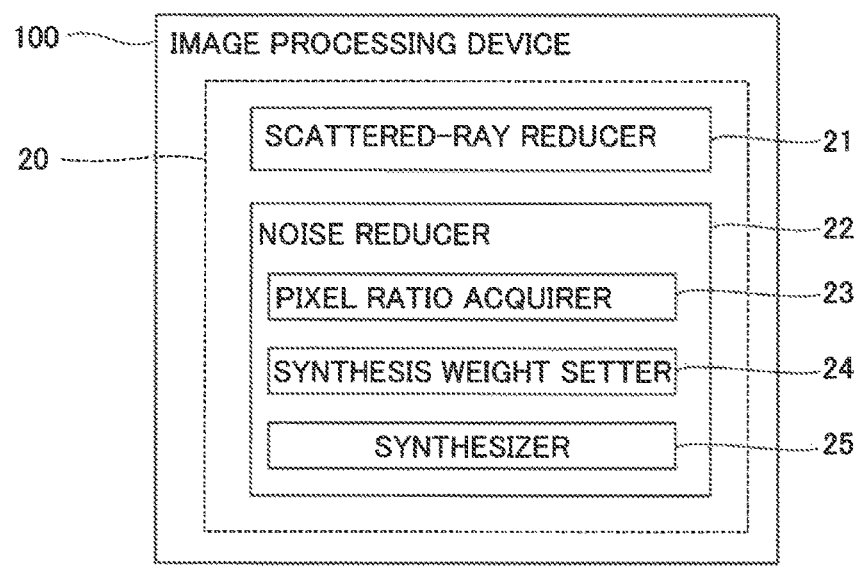
FIG. 2 is a block diagram of the image processing device according to the first embodiment.

As shown in FIG. 2, the image processing device 100 includes a computer that processes an X-ray image by executing an image processing program. For example, the image processing device 100 is configured as dedicated hardware in which a function of executing an image process is incorporated in a programmable logic device 20 such as a field-programmable gate array (FPGA). The image processing device 100 may include a CPU, a ROM, a RAM, etc. that are common to or separate from those of the controller 4. In that case, the image processing device 100 is configured in the form of software by causing the CPU to execute the image processing program. The image processing device 100 may be provided separately from the controller 4 as shown in FIG. 1, or may be incorporated as a portion of the controller 4.

In the first embodiment, the image processing device 100 includes a scattered-ray reducer 21 and a noise reducer 22. The scattered-ray reducer 21 and the noise reducer 22 can be configured as image processing modules incorporated in the logic device 20 such as an FPGA. The scattered-ray reducer 21 and the noise reducer 22 can be functional blocks that perform the image process and are configured in the form of software by causing the CPU to execute the image processing program.

When the subject P is irradiated with radiation, and the radiation is detected by the X-ray detector 3, the X-ray image includes direct-ray components caused by direct rays transmitted through the subject P, scattered-ray components caused by scattered rays generated by scattering in the subject P, and other noise components. The direct-ray components are image information that reflects the structure of the subject P. On the other hand, the scattered-ray components and the noise components do not include the structural information about the subject P, and degrade the image quality of the X-ray image. Therefore, in simple terms, the correction process by the image processing device 100 is a process for removing the scattered-ray components and the noise components from the X-ray image and extracting only the direct-ray components as much as possible.

The scattered-ray reducer 21 performs a process for reducing the scattered-ray components included in an X-ray image 51 (see FIG. 3) obtained by irradiating the subject P with radiation from the X-ray image 51. Specifically, the scattered-ray reducer 21 performs an estimation process for estimating the scattered-ray components included in the X-ray image 51, and a scattered-ray component reduction process for removing the estimated scattered-ray components from the X-ray image 51. The scattered-ray reducer 21 generates a scattered-ray reduced image 52 (see FIG. 3) in which the scattered-ray components have been reduced from the X-ray image 51.

The noise reducer 22 reduces the noise components included in the scattered-ray reduced image 52 obtained by reducing the scattered-ray components from the X-ray image 51. Specifically, the noise reducer 22 performs a process for reducing the noise components caused by statistical noise (quantum noise) included in a radiation image. The noise reducer 22 performs, on the scattered-ray reduced image 52 in which the scattered-ray components have been reduced by the scattered-ray reducer 21, a filtering process to reduce the noise components. The noise reducer 22 generates, by the filtering process, a noise reduced image 53 (see FIG. 3) in which the noise components have been reduced from the scattered-ray reduced image 52.

In the first embodiment, the noise reducer 22 includes a pixel ratio acquirer 23.

The pixel ratio acquirer 23 acquires a pixel value ratio $\alpha$ (see FIG. 4) between the scattered-ray reduced image 52 after reduction of the scattered-ray components and the X-ray image 51 before reduction of the scattered-ray components. The noise reducer 22 is configured to reduce the noise components from the scattered-ray reduced image 52 based on the pixel value ratio $\alpha$.

Specifically, the noise reducer 22 includes a synthesis weight setter 24 and a synthesizer 25.

Figure 4:
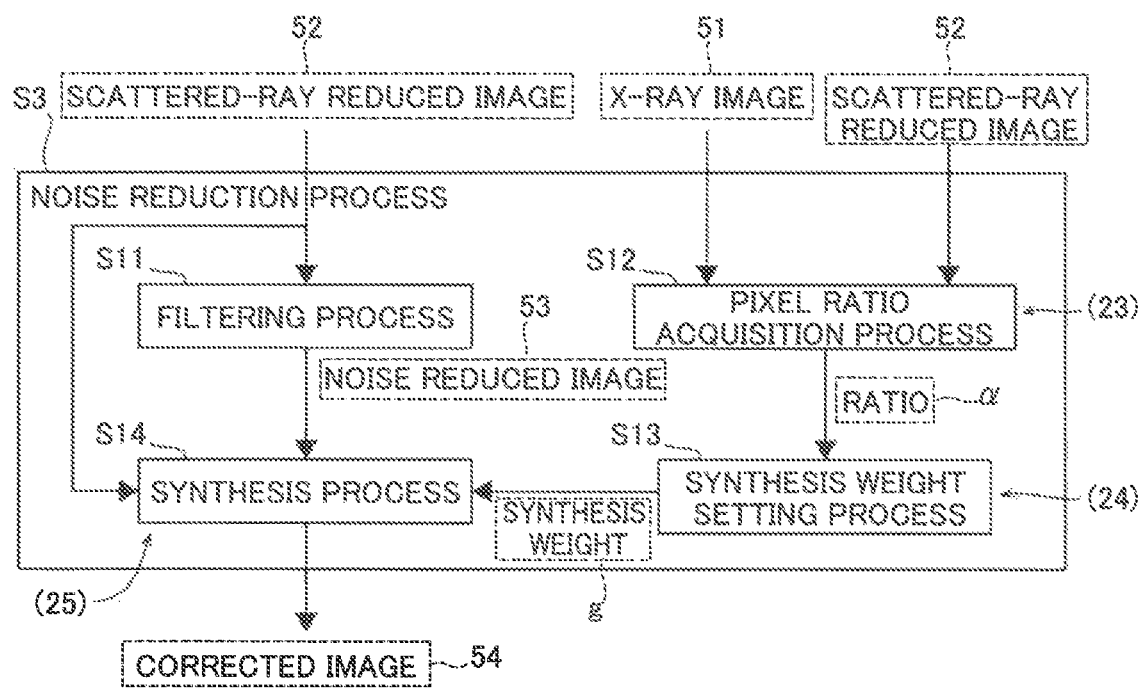
FIG. 4 is a diagram for illustrating the details of a noise reduction process.

The synthesis weight setter 24 sets a synthesis weight g based on the pixel value ratio $\alpha$ (see FIG. 4). The synthesizer 25 performs weighted synthesis on the noise reduced image 53 obtained by reducing the noise components from the scattered-ray reduced image 52 and the scattered-ray reduced image 52 with the set synthesis weight g (see FIG. 4). Accordingly, the noise reducer 22 performs weighted synthesis on the noise reduced image 53 and the scattered-ray reduced image 52 with the synthesis weight g set based on the pixel value ratio $\alpha$ to reduce the noise components from the scattered-ray reduced image 52.

In this manner, the image processing device 100 reduces the scattered-ray components and the noise components from the X-ray image 51 with the scattered-ray reducer 21 and the noise reducer 22. The image processing device 100 is configured to output a corrected image 54 (see FIG. 3) obtained by reducing the scattered-ray components and the noise components from the X-ray image 51 to the controller 4.

(X-Ray Image Processing)

A flow of an X-ray image process by the image processing device 100 is now described with reference to FIG. 3.

In step S1, the image processing device 100 acquires the X-ray image 51.

In step S2, the image processing device 100 performs the scattered-ray component estimation process and the scattered-ray component reduction process with the scattered-ray reducer 21. The scattered-ray reducer 21 generates the scattered-ray reduced image 52 after reduction of the scattered-ray components.

In the scattered-ray component estimation process and the scattered-ray component reduction process, as long as the scattered-ray components can be estimated from the X-ray image, and the estimated scattered-ray components can be reduced from the X-ray image, a processing method is not particularly limited. As an example of the estimation process, a method for regarding a pixel having a high luminance value (pixel value) of a low-frequency band component of an X-ray image as a scattered-ray component as described in U.S. Pat. No. 8,064,676 may be used. As another example, the scattered-ray components may be estimated by a convolution of the X-ray image and a point spread function, as described in Japanese Patent Laid-Open No. 9-149895. The scattered-ray components may be estimated by a method other than these exemplified methods and reduced from the X-ray image.

In step S3, the image processing device 100 performs the noise component reduction process with the noise reducer 22. The noise reducer 22 generates the corrected image 54 in which the scattered-ray components and the noise components have been reduced from the X-ray image 51. The noise component reduction process is described below in detail.

In step S4, the image processing device 100 outputs the corrected image 54 obtained by reducing the scattered-ray components and the noise components from the X-ray image 51 to the controller 4 (see FIG. 1).

(Noise Component Reduction Process)

Figure 3:
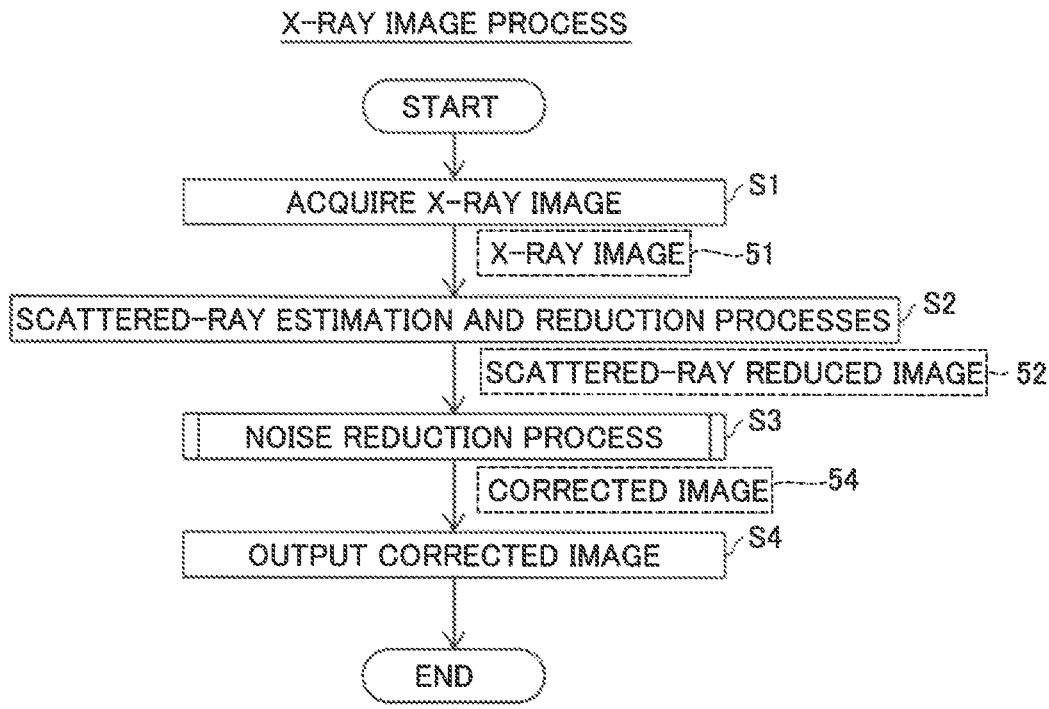
FIG. 3 is a flowchart for illustrating an X-ray image process according to the first embodiment.

The noise component reduction process shown in step S3 of FIG. 3 is now described with reference to FIGS. 4 to 8.

<Description of Noise Components>

Figure 5:
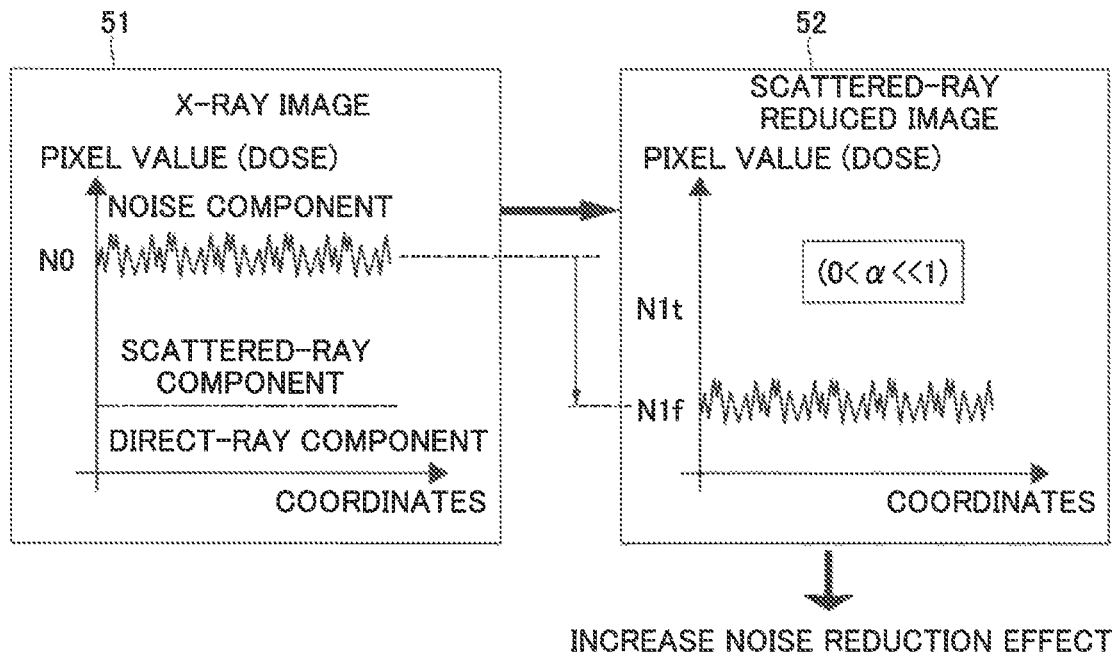
FIG. 5 is a diagram for illustrating a pixel value ratio in the case of a large scattered-ray component amount.

It is known that a noise component (statistical noise) amount in the X-ray image 51 has a positive correlation with the amount of radiation that has reached a detector (i.e., a pixel value of the radiation image). Therefore, as shown in FIG. 5, as an average pixel value NO in the X-ray image 51 increases, the statistical noise amount tends to increase. That is, the statistical noise amount increases as the total dose of direct rays and scattered rays increases.

A scattered-ray component amount in the X-ray image 51 varies depending on the body type (thickness) of the subject P, for example. In general, scattered rays tend to increase as the thickness of the subject P increases and a distance through which X-rays pass through the subject P increases.

Figure 6:
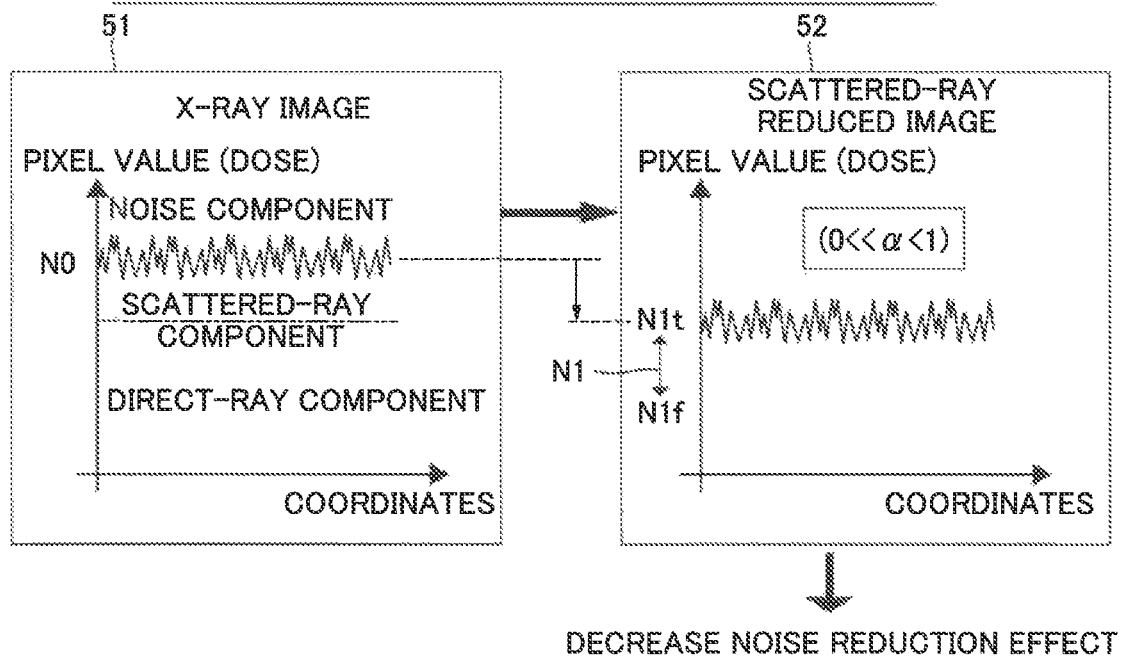
FIG. 6 is a diagram for illustrating a pixel value ratio in the case of a small scattered-ray component amount.

As shown in FIG. 5, when the scattered-ray component amount in the X-ray image 51 is large, a scattered-ray component amount to be removed increases, and thus the average pixel value N1$f$ of the scattered-ray reduced image 52 after reduction of the scattered-ray components decreases. As shown in FIG. 6, when the scattered-ray component amount in the X-ray image 51 is small, a scattered-ray component amount to be removed decreases, and thus the average pixel value N1$t$ of the scattered-ray reduced image 52 after reduction of the scattered-ray components increases. When the scattered-ray component amount in the X-ray image 51 is medium, the average pixel value N1 of the scattered-ray reduced image 52 after reduction of the scattered-ray components is between N1$t$ and N1$f$.

As described above, the amount of statistical noise correlates with the average pixel value NO in the X-ray image 51 whereas the average pixel value N1 of the scattered-ray reduced image 52 varies depending on the scattered-ray component amount included in the X-ray image 51, and thus when the scattered-ray component amount is large (average pixel value N1$f$), the noise component amount in the scattered-ray reduced image 52 is relatively large, and when the scattered-ray component amount is small (average pixel value Nit), the noise component amount in the scattered-ray reduced image 52 is relatively small.

Thus, it is preferable to appropriately control the noise reduction effect by the filtering process according to the scattered-ray component amount. Therefore, the noise reducer 22 is configured to adjust the noise reduction effect based on a ratio of pixel values before and after the scattered-ray component reduction process in the X-ray image by executing processes in step S11 to step S14 shown in FIG. 4 as the noise component reduction process in step S3.

<Filtering Process>

In step S11 in FIG. 4, the noise reducer 22 generates the noise reduced image 53 by performing, on the scattered-ray reduced image 52, the filtering process to reduce the noise components. The filtering process is a smoothing process. As long as the filtering process can smooth noise components superimposed on an image to be processed, a processing method is not particularly limited. As an example of the filtering process, general Gaussian filtering can be used. As an example of the filtering process, bilateral filtering or anisotropic filtering known as edge preserving filtering may be used.

The Gaussian filtering, the bilateral filtering, and the anisotropic filtering are used for a smoothing process in one image, and can be mainly applied to a still image. In the case of a moving image, smoothing is performed between time-series frame images. As the filtering process for the moving image, time integration filtering such as recursive filtering can be used. When the subject P or the region of interest in the subject P moves in the moving image, corresponding portions of the frame images are detected using a moving object tracking process by image recognition, and time integration filtering may be applied for each partial region in the image.

<Acquisition of Pixel Ratio>

In step S12, the pixel ratio acquirer 23 calculates the ratio $\alpha$ of the pixel values of the same pixel between the X-ray image 51 and the scattered-ray reduced image 52 (pixel ratio acquisition process). For example, the pixel ratio acquirer 23 calculates the pixel value ratio $\alpha$ using the following formula (1).

$$\alpha(x,y)=Sc(x,y)/In(x,y) \quad (1)$$

where (x, y) represents the coordinates of a pixel in each image (0≤x≤X, 0≤y≤Y), X and Y represent the horizontal and vertical sizes (number of pixels) of the image, respectively, Sc(x, y) represents a pixel value at the coordinates (x, y) in the scattered-ray reduced image 52, In(x, y) represents a pixel value at the coordinates (x, y) in the X-ray image 51 before scattered-ray reduction, Sc(x, y)≤In(x, y), and α(x, y) is a variable satisfying 0≤α≤1.

<Synthesis Weight Setting Process>

In step S13, the synthesis weight setter 24 sets the synthesis weight g based on the pixel value ratio $\alpha$ (synthesis weight setting process). For example, the synthesis weight setter 24 calculates the synthesis weight g using the following formula (2).

$$g(x,y)=F(\alpha(x,y)) \quad (2)$$

where F represents a conversion function using a as a variable, and the synthesis weight g(x, y) is a variable satisfying 0≤g≤1.

The conversion function F may be a linear function or a non-linear function. As an example of the linear function, there is the following formula (3), for example. As an example of the non-linear function, there is the following equation (4), for example.

$$F(k)=ak+b \quad (3)$$

$$F(k)=ak^2+bk^1+ck^{-1}+d \quad (4)$$

where the pixel value ratio α(x, y) is substituted for a variable k, and a, b, c, and d are parameters (coefficients) that determine the conversion function F.

The synthesis weight g represents the weight of the scattered-ray reduced image 52 at the time of performing weighted synthesis on the scattered-ray reduced image 52 and the noise reduced image 53 using a formula (6) described below. In other words, as the synthesis weight g increases (is closer to 1), the percentage of the noise reduced image 53 in a synthesis process decreases (the percentage of the scattered-ray reduced image 52 increases), and as the synthesis weight g decreases (is closer to 0), the ratio of the noise reduced image 53 in the synthesis process increases (the ratio of the scattered-ray reduced image 52 decreases).

As shown in FIGS. 5 and 6, as the scattered-ray component amount in the X-ray image before reduction increases, the pixel value ratio α decreases, but the noise component amount in the scattered-ray reduced image 52 relatively increases. Conversely, as the scattered-ray component amount in the X-ray image before reduction decreases, the pixel value ratio α increases, but the noise component amount in the scattered-ray reduced image 52 relatively decreases.

Therefore, the synthesis weight setter 24 sets the synthesis weight g in such a manner that as the pixel value ratio α of the scattered-ray reduced image 52 to the X-ray image 51 decreases, the weight of the noise reduced image 53 increases. That is, as shown in FIG. 7, the conversion function F is set in such a manner that the value of a decreases, the value of g decreases.

Figure 7:
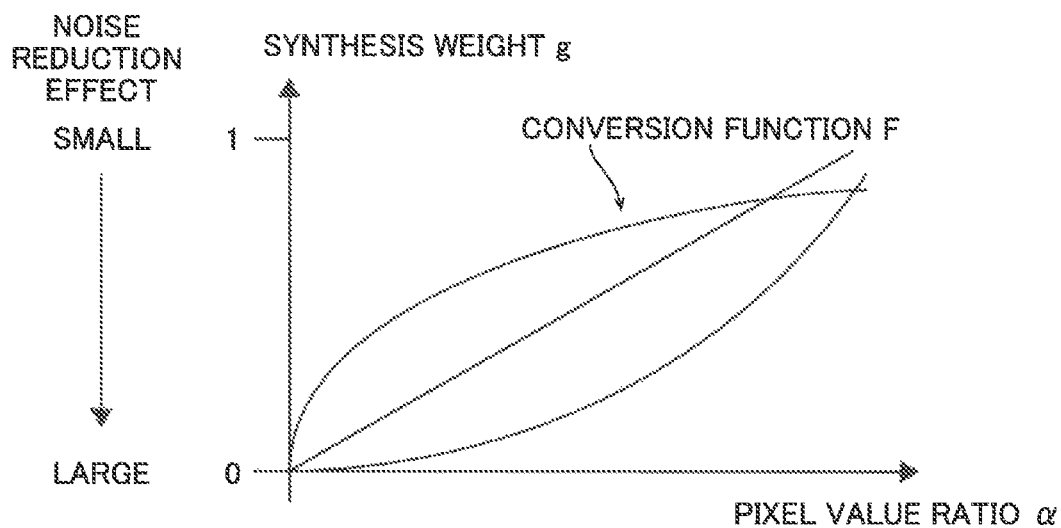
FIG. 7 is a diagram showing an example of a conversion function between the pixel value ratio and a synthesis weight.

FIG. 7 is a diagram showing a curve, which represents the conversion function F, with the vertical axis representing the synthesis weight g and the horizontal axis representing the pixel value ratio α. In other words, the conversion function F, in which the value of g decreases as the value of a decreases, is a function that monotonically increases the value of g with respect to the value of a. FIG. 7 illustrates three types of typical conversion functions F: a linear function, an n-th function (n is an integer of 2 or more), and a function of a power root. With any one of these conversion functions F, the synthesis weight g corresponding to the percentage of the noise components in the scattered-ray reduced image 52 can be set.

Figure 8:
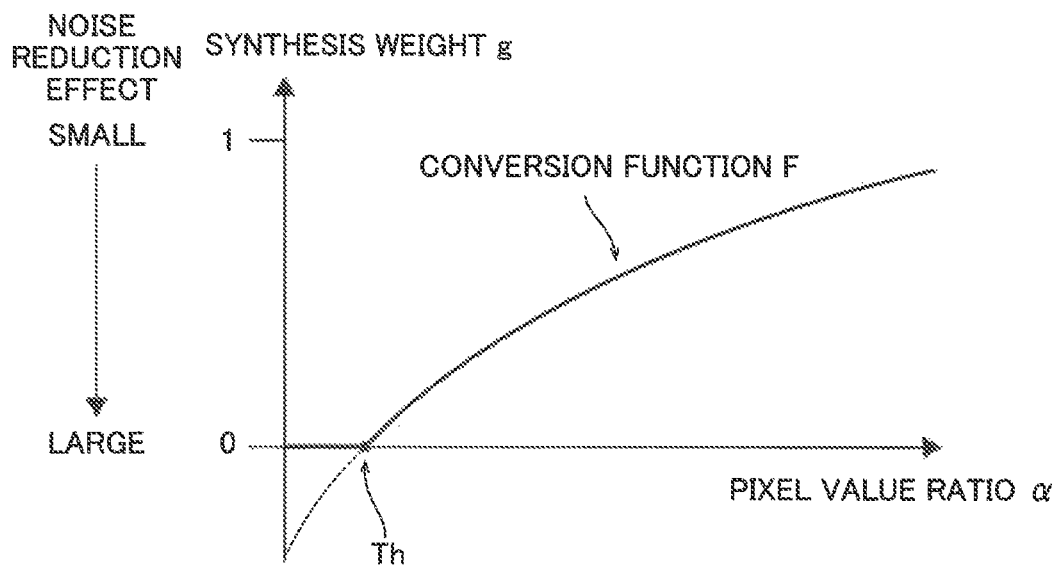
FIG. 8 is a diagram showing an example of a conversion function having a range in which the synthesis weight is zero.

In the first embodiment, as shown in FIG. 8, the synthesis weight setter 24 is preferably configured to set the weight of the scattered-ray reduced image 52 to zero when the pixel value ratio α of the scattered-ray reduced image 52 to the X-ray image 51 is smaller than a threshold.

Regardless of the scattered-ray component amount, the power (noise removal effect) of the filtering process is fixed. In this case, even when the scattered-ray component amount is particularly large, it is not possible to obtain the noise removal effect exceeding the power of the filtering process. On the other hand, when the power of the filtering process is set too high, the direct-ray components other than the noise components are also removed, and thus it is not appropriate to increase the power of the filtering process indefinitely. Therefore, when the pixel value ratio α is equal to or smaller than a threshold Th and the noise component amount is relatively large, the synthesis weight g is set to 0, and the ratio of the noise reduced image 53 in the synthesis process is set to 1. That is, in the filtering process, the power is set to a predetermined power that does not excessively remove the direct-ray components, and when the pixel value ratio α is equal to or smaller than the threshold Th, the noise reducer 22 outputs the noise reduced image 53 as the corrected image 54. Thus, even when the scattered-ray component amount is large, removal of the direct-ray components by excessive filtering is significantly reduced or prevented.

A specific example of the conversion function F according to the first embodiment shown in FIG. 8 is shown as the following formula (5).

$$F(k)=ak^{1/2}+b \quad (5)$$

where the conversion function F is (0≤F(k)≤1), and includes a region in which F(k) is 0 within a range equal to or smaller than the threshold Th (when k≤Th, F(k)=0). Appropriate values are set for the parameters a and b and the threshold Th according to the power of the filtering process.

<Synthesis Process>

As shown in FIG. 4, in step S14, the synthesizer 25 performs weighted synthesis on the noise reduced image 53 and the scattered-ray reduced image 52 with the synthesis weight g set based on the pixel value ratio α (synthesis process). As a result of the weighted synthesis, the synthesizer 25 generates the corrected image 54.

Specifically, the synthesizer 25 performs weighted synthesis on the noise reduced image 53 and the scattered-ray reduced image 52 using the following formula (6).

$$Out(x,y)=g(x,y)\times Sc(x,y)+\{1-g(x,y)\}\times Sm(x,y) \quad (6)$$

where Out(x, y) represents a pixel value at the coordinates (x, y) in the corrected image 54, and Sm(x, y) represents a pixel value at the coordinates (x, y) in the noise reduced image 53.

As shown in the above formula (6), the synthesizer 25 acquires the scattered-ray reduced image 52 after the scattered-ray reduction process and the noise reduced image 53 after the filtering process on the scattered-ray reduced image 52, and acquires the synthesis weight g set by the synthesis weight setter 24. The synthesizer 25 synthesizes the scattered-ray reduced image 52 and the noise reduced image 53 at a ratio according to the synthesis weight g.

Consequently, as the pixel value ratio α is smaller and the synthesis weight g is set smaller, the synthesis ratio of the noise reduced image 53 increases. In this manner, the noise reducer 22 adjusts the noise removal effect according to the ratio of the noise components in the scattered-ray reduced image 52 by adjusting the synthesis ratio of the noise reduced image 53. As described above, when the pixel value ratio α is equal to or smaller than the threshold Th, the synthesis weight g is set to 0, and thus the synthesis ratio of the scattered-ray reduced image 52 in the above formula (5) becomes 0. Consequently, the noise reducer 22 outputs the noise reduced image 53 as the corrected image 54 when the pixel value ratio α is equal to or smaller than the threshold Th.

(Example of Image Process)

Figure 9:
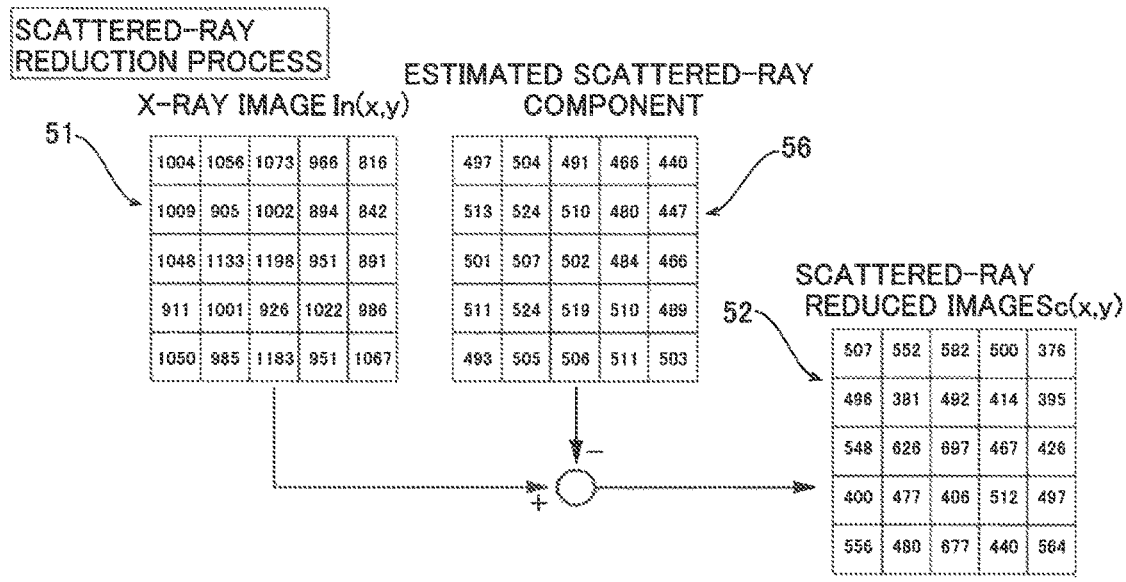
FIG. 9 is a schematic view for illustrating a specific example of a scattered-ray reduction process.
Figure 10:
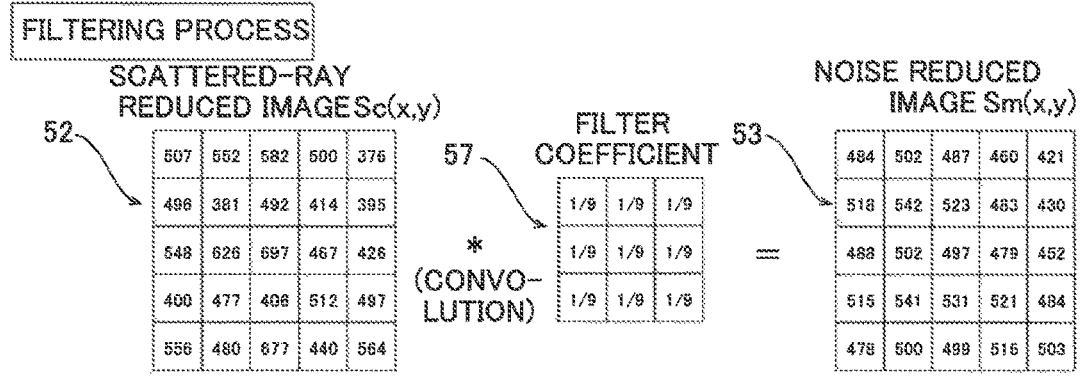
FIG. 10 is a schematic view for illustrating a specific example of a filtering process.
Figure 11:
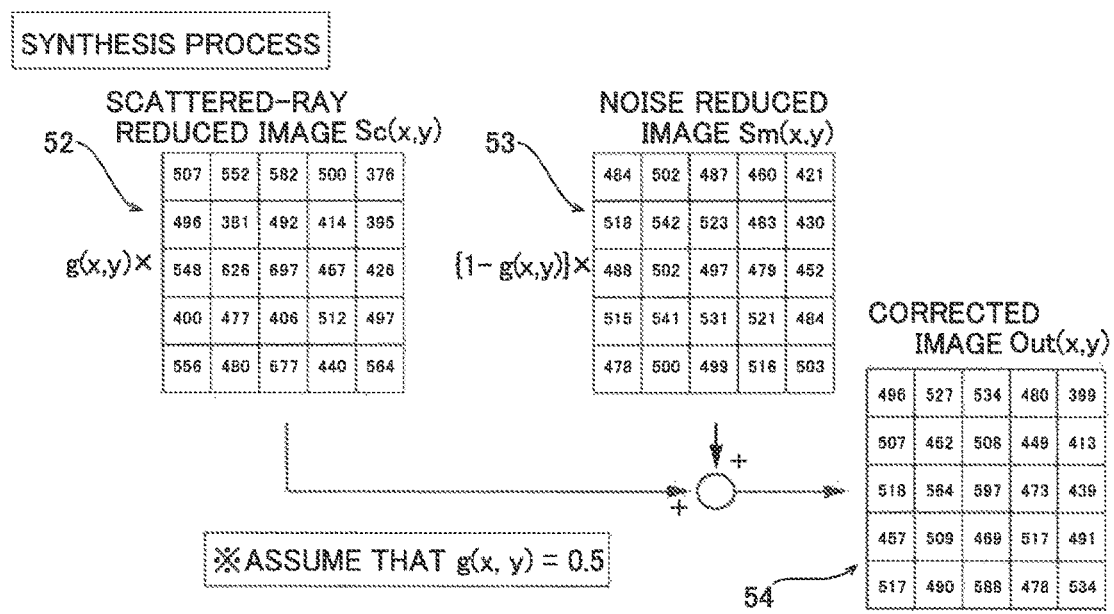
FIG. 11 is a schematic view for illustrating a specific example of a synthesis process.

The image process performed by the image processing device 100 according to the first embodiment is now described in a simplified manner with reference to FIGS. 9 to 11. FIGS. 9 to 11 show an example in which the image process is performed on an X-ray image of 5×5 pixels for convenience. Each of the 5×5 rectangular regions shown in the figures is a pixel, and a numerical value in the pixel indicates a pixel value.

FIG. 9 shows the scattered-ray reduction process. Scattered-ray components 56 are estimated for each pixel of the X-ray image 51 by the scattered-ray reducer 21. The scattered-ray reducer 21 generates the scattered-ray reduced image 52 by dividing the estimated scattered-ray components 56 from the X-ray image 51 for each pixel.

FIG. 10 shows the filtering process. The filtering process is performed on the scattered-ray reduced image 52 by the noise reducer 22 to generate the noise reduced image 53. The noise reducer 22 performs a convolution using a preset kernel (filter coefficient) 57 on the scattered-ray reduced image 52 to calculate the noise reduced image 53. For convenience, an example is shown in which the kernel uses a uniform moving-average filter. In the case of another filter such as a Gaussian filter or a bilateral filter, a corresponding kernel is set.

FIG. 11 shows the synthesis process. Weighted synthesis using the synthesis weight g is performed on the scattered-ray reduced image 52 and the noise reduced image 53 by the synthesizer 25 to generate the corrected image. For convenience, an example is shown in which the synthesis weight g is assumed to be 0.5, which is constant for all pixels. The synthesizer 25 calculates a pixel value after synthesis by summing (see the above formula (6)) values obtained by multiplying corresponding pixels (xy coordinates) of the scattered-ray reduced image 52 and the noise reduced image 53 by each weight. Consequently, the corrected image 54 is obtained.

Note that, as can be seen from the above formulas (2) and (5), in actuality, the weight g is individually set for each pixel according to the pixel value ratio α of the corresponding pixels of the scattered-ray reduced image 52 and the noise reduced image 53. The synthesizer 25 performs weighted synthesis using the corresponding weight g for each pixel.

In the above manner, the image process is performed by the image processing device 100 according to the first embodiment.

Advantages of First Embodiment

According to the first embodiment, the following advantages are obtained.

According to the first embodiment, as described above, the noise reducer 22 includes the pixel ratio acquirer 23 configured to acquire the pixel value ratio α between the scattered-ray reduced image 52 after reduction of the scattered-ray components and the X-ray image 51 before the reduction of the scattered-ray components, and is configured to reduce the noise components from the scattered-ray reduced image 52 based on the pixel value ratio α. As described above, the statistical noise has a correlation with the pixel value of the X-ray image 51, and thus the scattered dose can be associated with the noise component amount (noise component amount to be reduced) according to the scattered dose using the pixel value ratio α between the scattered-ray reduced image 52 and the X-ray image 51. Therefore, the noise components can be appropriately reduced from the X-ray image 51 by a simple process based on the pixel value ratio α. Thus, unlike the related art, it is not necessary to separately acquire noise statistics from the X-ray image and the scattered-ray reduced image, and the noise components can be simply reduced based on the pixel value ratio α between the X-ray image 51 and the scattered-ray reduced image 52. Consequently, the noise reduction process can be simplified, and can be performed at high speed and at low computational cost.

According to the first embodiment, as described above, the noise reducer 22 includes the synthesis weight setter 24 configured to set the synthesis weight g based on the pixel value ratio α, and the synthesizer 25 configured to perform weighted synthesis on the noise reduced image 53 obtained by reducing the noise components from the scattered-ray reduced image 52 and the scattered-ray reduced image 52 using the set synthesis weight g. Accordingly, when the noise reduction effect is weakened, the synthesis weight of the scattered-ray reduced image 52 is increased, and when the noise reduction effect is enhanced, the synthesis weight of the noise reduced image 53 is increased such that the degree of reduction of the noise components can be adjusted. Furthermore, the synthesis weight can be set according to the noise component amount (noise component amount to be reduced) grasped based on the pixel value ratio α, and thus an appropriate noise reduction process can be performed according to the noise component amount included in the scattered-ray reduced image 52 while the computational cost is reduced based on the pixel value ratio α.

According to the first embodiment, as described above, the synthesis weight setter 24 is configured to set the synthesis weight g in such a manner that as the pixel value ratio α of the scattered-ray reduced image 52 to the X-ray image 51 decreases, the weight of the noise reduced image 53 increases. Accordingly, as the pixel value ratio α of the scattered-ray reduced image 52 to the X-ray image 51 is smaller, synthesis is performed with the larger weight of the noise reduced image 53 such that the noise components can be effectively reduced according to the noise component amount.

According to the first embodiment, as described above, the synthesis weight setter 24 is configured to set the weight of the scattered-ray reduced image 52 to zero when the pixel value ratio α of the scattered-ray reduced image 52 to the X-ray image 51 is smaller than the threshold Th. Accordingly, when the noise component amount is so large that the pixel value ratio α is smaller than the threshold Th, the noise reduced image 53 is directly output such that the limit of the noise reduction effect can be set in a range in which the image quality is not excessively reduced without increasing the computational cost.

Second Embodiment

A second embodiment of the present invention is now described with reference to FIGS. 12 to 15. In the second embodiment, an example is described in which the noise reduction process according to the first embodiment is performed for each band image by frequency-decomposing an X-ray image into a plurality of band images. In the second embodiment, description of the same configurations as those of the first embodiment is omitted.

(Configuration of Image Processing Device)

Figure 12:
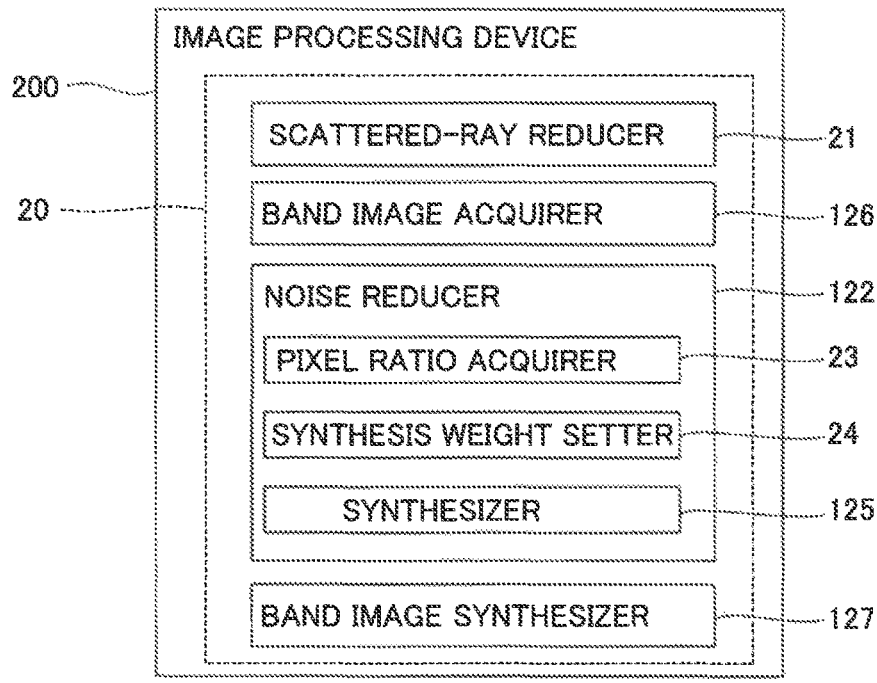
FIG. 12 is a block diagram of an image processing device according to a second embodiment.

As shown in FIG. 12, an image processing device 200 according to the second embodiment further includes a band image acquirer 126 and a band image synthesizer 127 in addition to a scattered-ray reducer 21 and a noise reducer 122. The band image acquirer 126 and the band image synthesizer 127 can be configured as image processing modules incorporated in a logic device 20, similarly to the scattered-ray reducer 21 and the noise reducer 122, and can be functional blocks that perform an image process and are configured in the form of software.

The band image acquirer 126 is configured to frequency-decompose a scattered-ray reduced image 52 to acquire a plurality of band images 155 (see FIG. 13) of a plurality of frequency bands. As long as in the frequency decomposition, the scattered-ray reduced image 52 is decomposed into the plurality of band images 155 of a plurality of frequency bands, a processing method is not particularly limited. The bandwidth and the number of bands to be decomposed may be set according to the required image quality and processing speed, and are not particularly limited.

As frequency decomposition processing methods, there are Fourier transform, an image pyramid method, etc., for example. The Fourier transform is a process for converting image information in a spatial domain into a spatial frequency domain. Inverse Fourier transform is performed after components other than corresponding frequency components are removed in the spatial frequency domain such that a band image can be generated for each frequency band. The image pyramid method is a method for decomposing an original X-ray image into a plurality of images having different resolutions in a plurality of steps, and the respective images from high resolution to low resolution correspond to band images having different frequency bands.

Figure 13:
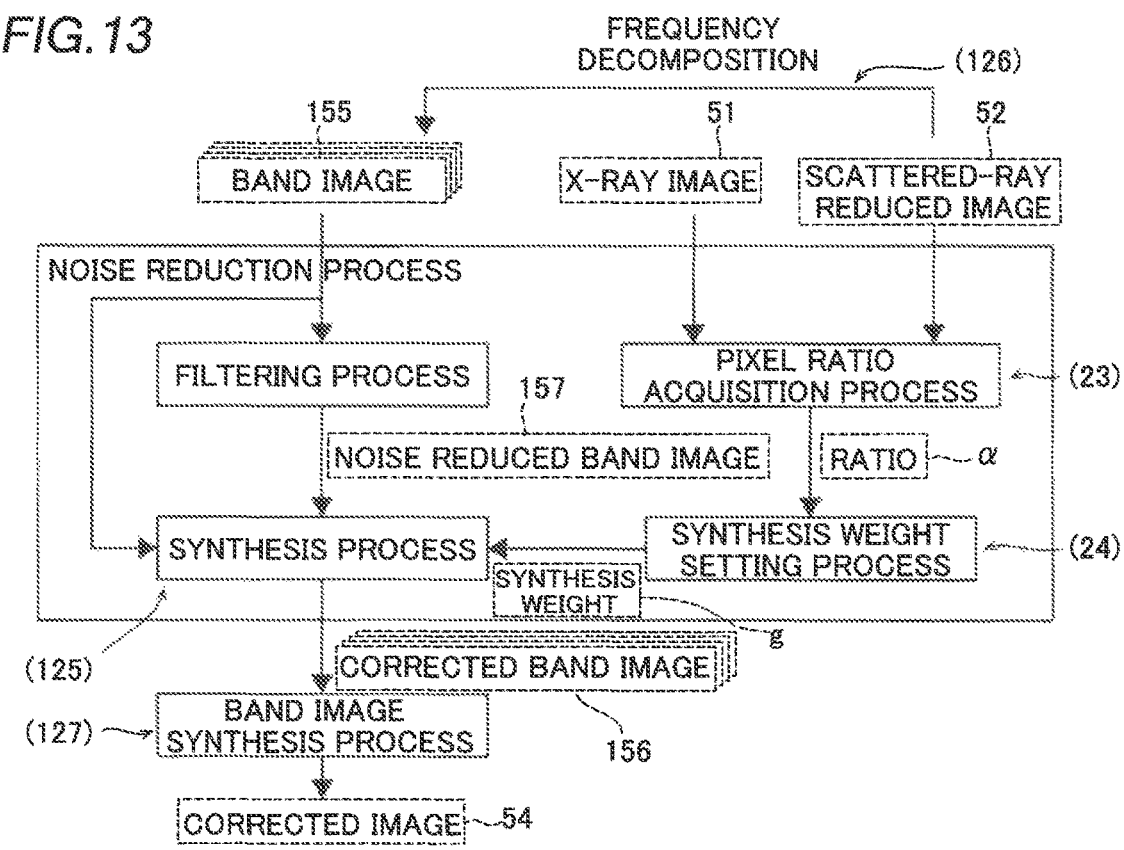
FIG. 13 is a diagram for illustrating a noise reduction process according to a second embodiment.

The band image synthesizer 127 is configured to synthesize a plurality of corrected band images 156 obtained by reducing noise components included in the plurality of band images 155. In the second embodiment, the noise reducer 122 is configured to reduce the noise components for each of the plurality of band images 155 based on a pixel value ratio α. That is, a noise reduction process is individually performed, by the noise reducer 122, on each band image 155 obtained by decomposition by the band image acquirer 126. As shown in FIG. 13, the band image synthesizer 127 generates a corrected image 54 by synthesizing the corrected band images 156 after the noise reduction process.

The image processing device 200 is configured to output the corrected image 54 on which frequency synthesis has been performed by the band image synthesizer 127.

As shown in FIG. 13, in the second embodiment, the noise reducer 122 includes a synthesis weight setter 24 that separately sets a synthesis weight g for each band image 155 based on the pixel value ratio α. Specifically, the synthesis weight setter 24 calculates the synthesis weight g of each band image 155 using a conversion function F preset for each frequency band.

Figure 14:
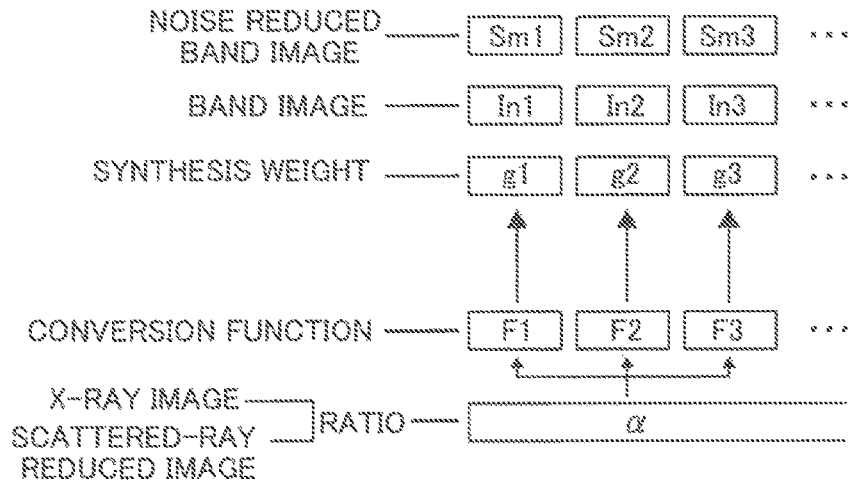
FIG. 14 is a schematic view for illustrating the correspondence between frequency-decomposed band images, conversion functions, and synthesis weights.

That is, as shown in FIG. 14, when band images In1, In2, In3, . . . are obtained by the frequency decomposition, the synthesis weight setter 24 acquires synthesis weights g1, g2, g3, . . . using conversion functions F1, F2, F3, . . . for respective frequency bands, respectively. For each of the conversion functions F, values of the parameters a to d can be made different using common functions as exemplified in the above formulas (3) to (5), for example. Thus, the different conversion functions F1, F2, F3, . . . are set for respective frequency bands.

For example, edge components of a structure that appears in the X-ray image are included in a high-frequency band, and information with little change such as DC components that appear in the X-ray image is included in a low-frequency band. It is preferable to ultimately determine the degree of noise removal in each band by reflecting the usage and the user tendency, and thus it is preferable to set some or all of the parameters of the conversion function F to be changeable. The parameters of each conversion function F may be fixed values.

In the second embodiment as well, a pixel ratio acquirer 23 acquires the pixel value ratio α between the X-ray image 51 before the frequency decomposition process and the scattered-ray reduced image 52. That is, the pixel value ratio α is common to each band image 155.

As shown in FIG. 13, a synthesizer 125 is configured to perform weighted synthesis (synthesis process) on a noise reduced image (hereinafter referred to as a noise reduced band image 157) obtained by reducing the noise components from each band image 155, and a corresponding band image 155 using the synthesis weight g set for each band image 155.

That is, the synthesizer 125 acquires the band images 155 (In1 to In3 in FIG. 15) and the noise reduced band images 157 (Sm1 to Sm3 in FIG. 15) after a filtering process on the band images 155, and acquires the synthesis weight g for each frequency band set by the synthesis weight setter 24. The synthesizer 125 synthesizes the band image 155 and the noise reduced band image 157 at a ratio according to the synthesis weight g of each frequency band. By the synthesis process, the synthesizer 125 generates the corrected band image 156 for each frequency band.

(X-Ray Image Process)

Figure 15:
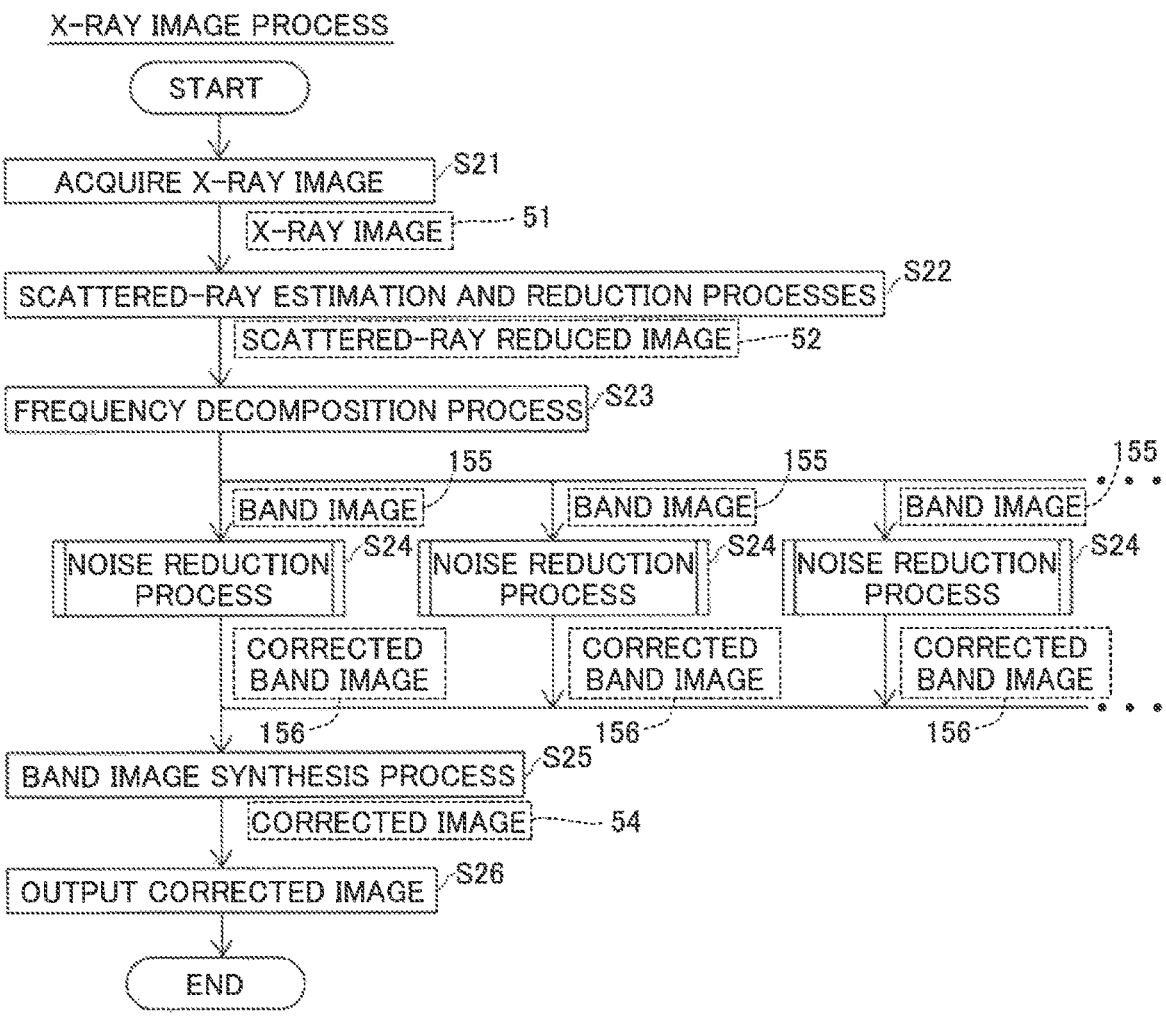
FIG. 15 is a flowchart for illustrating an X-ray image process according to the second embodiment.

A flow of an X-ray image process by the image processing device 200 according to the second embodiment is now described with reference to FIG. 15.

In step S21, the image processing device 200 acquires the X-ray image 51.

In step S22, the image processing device 200 performs a scattered-ray component estimation process and a scattered-ray component reduction process with the scattered-ray reducer 21. The scattered-ray reducer 21 generates the scattered-ray reduced image 52 after reduction of scattered-ray components.

In step S23, the image processing device 100 performs the frequency decomposition process on the scattered-ray reduced image 52 with the band image acquirer 126. The band image acquirer 126 decomposes the scattered-ray reduced image 52 into a predetermined number of band images 155.

In step S24, the image processing device 100 performs, by the noise reducer 122, a noise component reduction process on each of the band images 155 obtained by the frequency-decomposition. The noise reducer 122 generates the corrected band image 156 with reduced noise components for each frequency band.

In step S25, the image processing device 100 performs a process for synthesizing the corrected band images 156 for the respective frequency bands with the band image synthesizer 127. The band image synthesizer 127 generates the corrected image 54 by synthesis.

In step S26, the image processing device 100 outputs, to a controller 4, the corrected image 54 obtained by reducing the scattered-ray components and the noise components from the X-ray image 51.

The remaining configurations of the second embodiment are similar to those of the first embodiment.

Advantages of Second Embodiment

According to the second embodiment, the following advantages are obtained.

According to the second embodiment, similarly to the first embodiment, the noise reducer 122 is configured to reduce the noise components from the scattered-ray reduced image 52 based on the pixel value ratio α. Accordingly, unlike the related art, it is not necessary to separately acquire noise statistics from the X-ray image and the scattered-ray reduced image, and the noise components can be simply reduced based on the pixel value ratio α between the X-ray image 51 and the scattered-ray reduced image 52. Consequently, the noise reduction process can be simplified, and can be performed at high speed and at low computational cost.

According to the second embodiment, as described above, the image processing device 200 includes the band image acquirer 126 configured to frequency-decompose the scattered-ray reduced image 52 to acquire the plurality of band images 155 of the plurality of frequency bands, and the band image synthesizer 127 configured to synthesize the plurality of corrected band images 156 obtained by reducing the noise components included in each of the plurality of band images 155. Furthermore, the noise reducer 122 is configured to reduce the noise components for each of the plurality of band images 155 based on the pixel value ratio α. Accordingly, the noise reduction process based on the pixel value ratio α can be performed on each of the plurality of band images 155 for each band. Consequently, it is possible to obtain the corrected image 54 on which an appropriate noise reduction process has been performed for each frequency band.

According to the second embodiment, as described above, the noise reducer 122 includes the synthesis weight setter 24 configured to separately set the synthesis weight g for each band image 155 based on the pixel value ratio α, and the synthesizer 125 configured to perform weighted synthesis on the noise reduced image (noise reduced band image 157) obtained by reducing the noise components from each band image 155 and the corresponding band image 155 using the synthesis weight g set for each band image 155. Accordingly, the noise reduction effect can be adjusted for each band, and thus flexible image quality adjustment becomes possible.

The remaining advantages of the second embodiment are similar to those of the first embodiment.

Modified Examples

The embodiments disclosed this time must be considered as illustrative in all points and not restrictive. The scope of the present invention is not shown by the above description of the embodiments but by the scope of claims for patent, and all modifications (modified examples) within the meaning and scope equivalent to the scope of claims for patent are further included.

For example, while the example in which the subject is a human has been shown in each of the aforementioned first and second embodiments, the present invention is not limited to this. In the present invention, the subject may be a living thing other than a human or a thing. For example, the image processing device according to the present invention may be used for an image processing device for industrial equipment such as an X-ray inspection device (non-destructive inspection device) other than medical equipment such as an X-ray apparatus.

While the example in which the noise reducer 22 (122) includes the synthesis weight setter 24 and the synthesizer 25 (125), and the synthesis weight g is set according to the pixel value ratio α such that the noise removal effect is adjusted according to the pixel value ratio α has been shown in each of the aforementioned first and second embodiments, the present invention is not limited to this. For example, a plurality of types of filter coefficients (kernels) used for the filtering process may be set according to the noise component amount, and a filter (kernel) used for the filtering process may be selected according to the pixel value ratio α such that the noise removal effect is adjusted.

While the example in which the synthesis weight setter 24 is configured to set the weight of the scattered-ray reduced image 52 to zero when the pixel value ratio α is smaller than the threshold Th has been shown in each of the aforementioned first and second embodiments, the present invention is not limited to this. In the present invention, the threshold for fixing the synthesis weight to 0 may not be set for the pixel value ratio α. That is, the synthesis weight g may be changed over the entire range of the pixel value ratio α.

While the process operations of the image processing device according to the present invention are described using a flowchart in a flow-driven manner in which processes are performed in order along a process flow for the convenience of illustration in each of the first and second embodiments, the present invention is not limited to this. In the present invention, the process operations may be performed in an event-driven manner in which the processes are performed on an event basis. In this case, the process operations may be performed in a complete event-driven manner or in a combination of an event-driven manner and a flow-driven manner.

DESCRIPTION OF REFERENCE NUMERALS

21: scattered-ray reducer
22, 122: noise reducer
23: pixel ratio acquirer
24: synthesis weight setter
25, 125: synthesizer
51: X-ray image (radiation image)
52: scattered-ray reduced image
53: noise reduced image
54: corrected image
100, 200: image processing device
126: band image acquirer
127: band image synthesizer
155: band image
156: corrected band image
α: pixel value ratio
g: synthesis weight
P: subject
Th: threshold

The invention claimed is:
1. An image processing device comprising:
a scattered-ray reducer configured to reduce, from a radiation image, a scattered-ray component included in the radiation image obtained by irradiating a subject with radiation; and
a noise reducer configured to reduce a noise component included in a scattered-ray reduced image obtained by reducing the scattered-ray component from the radiation image; wherein
the noise reducer includes:
a pixel ratio acquirer configured to acquire a pixel value ratio which is a ratio of pixel values of the same pixel between the scattered-ray reduced image after reduction of the scattered-ray component and the radiation image before the reduction of the scattered-ray component; and
a synthesis weight setter configured to set, based on the pixel value ratio, a synthesis weight used for weighted synthesis of the scattered-ray reduced image and a noise reduced image obtained by reducing the noise component from the scattered-ray reduced image;
the noise reducer is configured to reduce the noise component from the scattered-ray reduced image by performing the weighted synthesis on the noise reduced image and the scattered-ray reduced image using the synthesis weight; and
the image processing device is configured to output a corrected image obtained by reducing the scattered-ray component and the noise component from the radiation image.

2. The image processing device according to claim 1, wherein the synthesis weight setter is configured to set the synthesis weight in such a manner that as the pixel value ratio of the scattered-ray reduced image to the radiation image decreases, a weight of the noise reduced image increases.

3. The image processing device according to claim 1, wherein the synthesis weight setter is configured to set a weight of the scattered-ray reduced image to zero when the pixel value ratio of the scattered-ray reduced image to the radiation image is smaller than a threshold.

4. An image processing device comprising:
a scattered-ray reducer configured to reduce, from a radiation image, a scattered-ray component included in the radiation image obtained by irradiating a subject with radiation;
a band image acquirer configured to frequency-decompose a scattered-ray reduced image obtained by reducing the scattered-ray component from the radiation image to acquire a plurality of band images of a plurality of frequency bands; and
a noise reducer configured to reduce a noise component included in each of the plurality of band images, the noise reducer including a synthesis weight setter configured to separately set a synthesis weight for each of the plurality of band images based on a pixel value ratio which is a ratio of pixel values of the same pixel between the scattered-ray reduced image after reduction of the scattered-ray component and the radiation image before the reduction of the scattered-ray component; wherein
the image processing device is configured to output a corrected image obtained by reducing the noise component included in each of the plurality of band images by performing weighted synthesis, using the synthesis weight set for each of the plurality of band images, on a noise reduced image obtained by reducing the noise component from each of the plurality of band images and a corresponding band image.

* * * * *